United States Patent [19]

Pryor

[11] Patent Number: 5,624,635
[45] Date of Patent: *Apr. 29, 1997

[54] METHOD AND APPARATUS FOR OZONE TREATMENT OF SOIL

[76] Inventor: Alan E. Pryor, 655 S. Fair Oaks Ave., Apt. I-304, Sunnyvale, Calif. 94086

[*] Notice: The term of this patent shall not extend beyond the expiration date of Pat. No. 5,566,627.

[21] Appl. No.: 512,777

[22] Filed: Aug. 9, 1995

Related U.S. Application Data

[63] Continuation of Ser. No. 184,333, Jan. 18, 1994, abandoned.
[51] Int. Cl.$^6$ .................................................. A61L 2/20
[52] U.S. Cl. ................................................ 422/32; 422/28
[58] Field of Search ............................. 239/201, 207; 422/28, 32, 292; 405/51

[56] References Cited

U.S. PATENT DOCUMENTS

| | | | |
|---|---|---|---|
| 3,413,940 | 12/1968 | Vissers . | |
| 4,293,237 | 10/1981 | Robey et al. | 405/51 X |
| 4,549,477 | 10/1985 | McCabe, Jr. | 99/477 |
| 4,570,553 | 2/1986 | Ito | 111/6 |
| 4,632,044 | 12/1986 | Allen | 111/7 |
| 4,819,374 | 4/1989 | Gemgnani | 47/58 |
| 4,978,508 | 12/1990 | Hansen et al. | 422/186.08 |
| 5,011,599 | 4/1991 | Kearney et al. | 210/130 |
| 5,011,699 | 4/1991 | Mitsuda et al. | 426/320 |
| 5,040,729 | 8/1991 | Carrozza | 239/201 |
| 5,053,140 | 10/1991 | Hurst | 210/704 |
| 5,221,312 | 6/1993 | Buhidar | 71/12 |
| 5,246,309 | 9/1993 | Hobby | 435/266 X |
| 5,259,962 | 11/1993 | Later | 210/758 |
| 5,269,943 | 12/1993 | Wickramanayake | 422/29 X |
| 5,277,655 | 1/1994 | Storkan et al. | 454/143 |

OTHER PUBLICATIONS

"Disinfection, Sterilization, and Preservation", Third Edition, Seymour S. Block, Lea & Febiger, 1983, p. 673.
Katan, J., et al., "The Weakening Effect as a Trigger for Biological Control and Criteria for its Evaluation," Biological Control of Plant Diseases, Plenum Press, New York, 1992, pp. 55–61.
Vargas, R., et al., Journal-of-General-and-Applied-Microbiology, 1991, 37:6, pp. 515–518.
Dropkin, V., "Introduction to Plant Nematology," John Wiley & Sons, 266, 270–271, p. 278, 1992.
Decker, H., "Plant Nematodes and Their Control (Phytonematology)," Kolos Publishers, 1972, p. 128.
Womersley, C., "Entomopathogenic Nematodes in Biological Control," CRC Press, p. 117, 1991.

(List continued on next page.)

Primary Examiner—Robert J. Warden
Assistant Examiner—E. Leigh Dawson
Attorney, Agent, or Firm—Skjerven, Morrill, MacPherson, Franklin & Friel; Alan H. MacPherson; Omkar K. Suryadevara

[57] ABSTRACT

An ozone containing gas is injected into soil, preferably substantially uniform in consistency, to kill biological life forms. A soil injector is used to inject ozone containing gas from an ozone supplier. In one embodiment, the ozone supplier is moved over the field by a structure such as a trailer or a vehicle. In another embodiment, a lattice arrangement of conduits is used to inject the ozone containing gas into the soil. The soil is optionally covered with a gas semipermeable or impermeable membrane subsequent to or prior to injection of the ozone containing as. In yet another embodiment, the soil is transferred to a chamber and subjected to in-vitro ozone treatment. In accordance with this invention, the soil is exposed to a sufficient concentration of ozone for a sufficient period of time such that the ozone oxidizes the impurities resulting in sanitization and a reduction of detrimental organisms.

17 Claims, 8 Drawing Sheets

OTHER PUBLICATIONS

Mignard, E. and Benet, J., "Diffusion of methyl bromide in soil," *Journal of Soil Science*, 1989, 40, pp. 151–165.

Encyclopedia of Chemical Technology, vol. 16, Third Edition, John Wiley & Sons, Inc., 1991, pp. 683–713.

Lembright, H., "Soil Fumigation: Principles and Application Technology," Supplement to Journal of Nematology, 22, pp. 632–644, Oct. 1990.

Alan Pryor, "Ozone Toxicology, Exposure Threshold Limit Values, and Safety Precautions," *Ozone News, International Ozone Association*, vol. 18, No. 6, pp. 1–8, Nov./Dec. 1990.

Synthesis Report of the Methyl Bromide Interim Scientific Assessment and Methyl Bromide Interim Technology and Economic Assessment requested by: United Nations Environment Programme, pp. 1–3 and 26, 27, and 31, Jun., 1992.

Patrick Cavanaugh, "Methyl Bromide Users Endure Changes," *Nut Grower*, pp. 12–14, Sep., 1993.

Patrick Cavanaugh, "Methyl Bromide Use Questioned," *Vegetable*, pp. 6–7, Sep./Oct., 1992.

An article on one page from *Vegetable*, Summer, 1993, entitled "Methyl Bromide Alternative Probed".

Larry Waterfield, "No Quick Fix for Methyl Bromide," *The Grower*, Nov., 1992.

F. Pauwels, "Soil Disinvestation in the Belgian Horticulture: A Practice View," 2 pages, publication and year unknown.

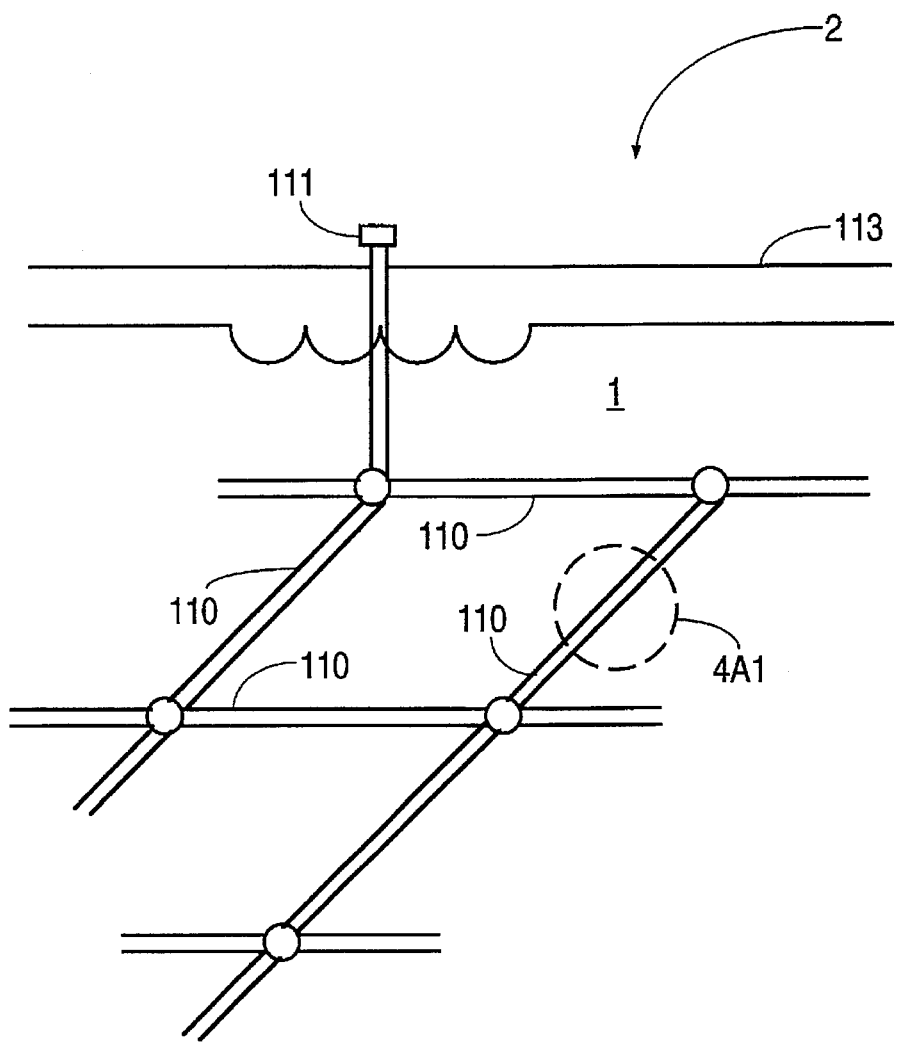
FIG. 4A
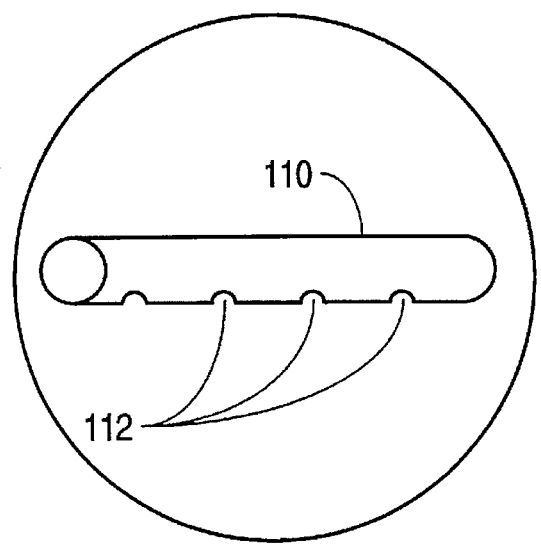
FIG. 4A1

METHOD AND APPARATUS FOR OZONE TREATMENT OF SOIL

This application is a continuation of application Ser. No. 08/184,333, filed Jan. 18, 1994 now abandoned.

FIELD OF THE INVENTION

This invention relates to a method and apparatus for treatment of soil to oxidize impurities and, in particular, to a method and apparatus for exposing soil to an ozone containing gas to reduce the level of undesirable biological organisms in the soil including, but not limited to, micro organisms, multicellular animals, plants and seeds.

BACKGROUND OF THE INVENTION

One common and effective commercially used disinfecting agent for treatment of soil is methyl bromide. Methyl bromide effectively destroys living cells once methyl bromide is transported across the cell wall. However, methyl bromide is being phased out of use due to its deleterious effect on the ozone layer and due to its human health hazards. Thus a substitute for methyl bromide is urgently needed.

Ozone in aqueous solutions has been used for inhibition or reduction of biological life forms such as molds, fungi, bacteria, algae, in numerous applications including swimming pools, potable water, bottled water, aquaria, fish hatcheries, and cooling towers. In the gas phase, ozone has been used primarily in the food processing industries for treatment of, for example, fish, grains, delicate vegetables, and processed foods. Gaseous ozone has also been used as a sanitizing agent for operating rooms, animal containment facilities, and air conditioning and heating ventilation systems and for deodorization in municipal waste treatment plants.

However, ozone has not reportedly been used to sanitize the soil in a field. Ozone in aqueous solutions has the drawback of slow dispersion of water into and through the soil of a field. Furthermore, aqueous ozone solutions suffer from rapid breakdown of ozone and the resultant difficulty in maintaining sufficiently high concentrations of ozone in the water in the soil. Ozone in aqueous solutions has a half life on the order of minutes in ambient conditions.

Although gaseous ozone has a half life on the order of hours (up to 20 hours depending on ambient conditions), gaseous ozone has not been traditionally used to sanitize soil in a field. According to traditional thinking, if gaseous ozone were used for soil treatment, ozone would rapidly break down by dissolving in the water entrapped in the soil. It was also thought that gaseous ozone dispersion is inhibited by the compacted, compressed nature of soil in a field and that untoward emissions of ozone gas from the soil in a field into the atmosphere minimized ozone's effectiveness.

SUMMARY OF THE INVENTION

This invention relates to a method and apparatus for use of ozone to treat soil. Ozone ($O_3$) is a powerful oxidizing agent. Ozone has 150% of the oxidation potential of chlorine and almost twice the oxidation potential of bromine. Unlike chlorine or bromine or halogenated compounds, ozone has a negligible deleterious effect on the environment because ozone breaks down into simple diatomic oxygen on reaction with an organic or inorganic agent. Moreover, ozone also readily self-destructs into simple diatomic oxygen due to its inherent instability.

In an ozone treatment method and apparatus in accordance with this invention, after the soil has been rendered or ensured to be relatively uniformly homogeneous in texture, an ozone containing gas from an ozone supplier is injected through a soil injector into the soil in a field. The ozone supplier is moved over the field by a structure such as a trailer or a vehicle. The ozone supplier is an ozone containing chamber in one embodiment and a corona ozone generator in another embodiment.

In another embodiment, the ozone containing gas is injected into the soil using a buried lattice arrangement of conduits. The soil is optionally covered with a gas impermeable or semi-impermeable membrane subsequent to or prior to injection of the ozone containing gas. In yet another embodiment, the soil is transferred to a chamber and subjected to in-vitro ozone treatment. The soil is exposed to ozone for a sufficient period of time such that the ozone oxidizes impurities in the soil.

This invention will be more fully understood in view of the following detailed description together with the drawings.

BRIEF DESCRIPTION OF THE DRAWING

FIGS. 4A and 4B illustrate other embodiments of this invention for injecting an ozone containing gas into the soil.

DETAILED DESCRIPTION OF THE INVENTION

Figure 1:
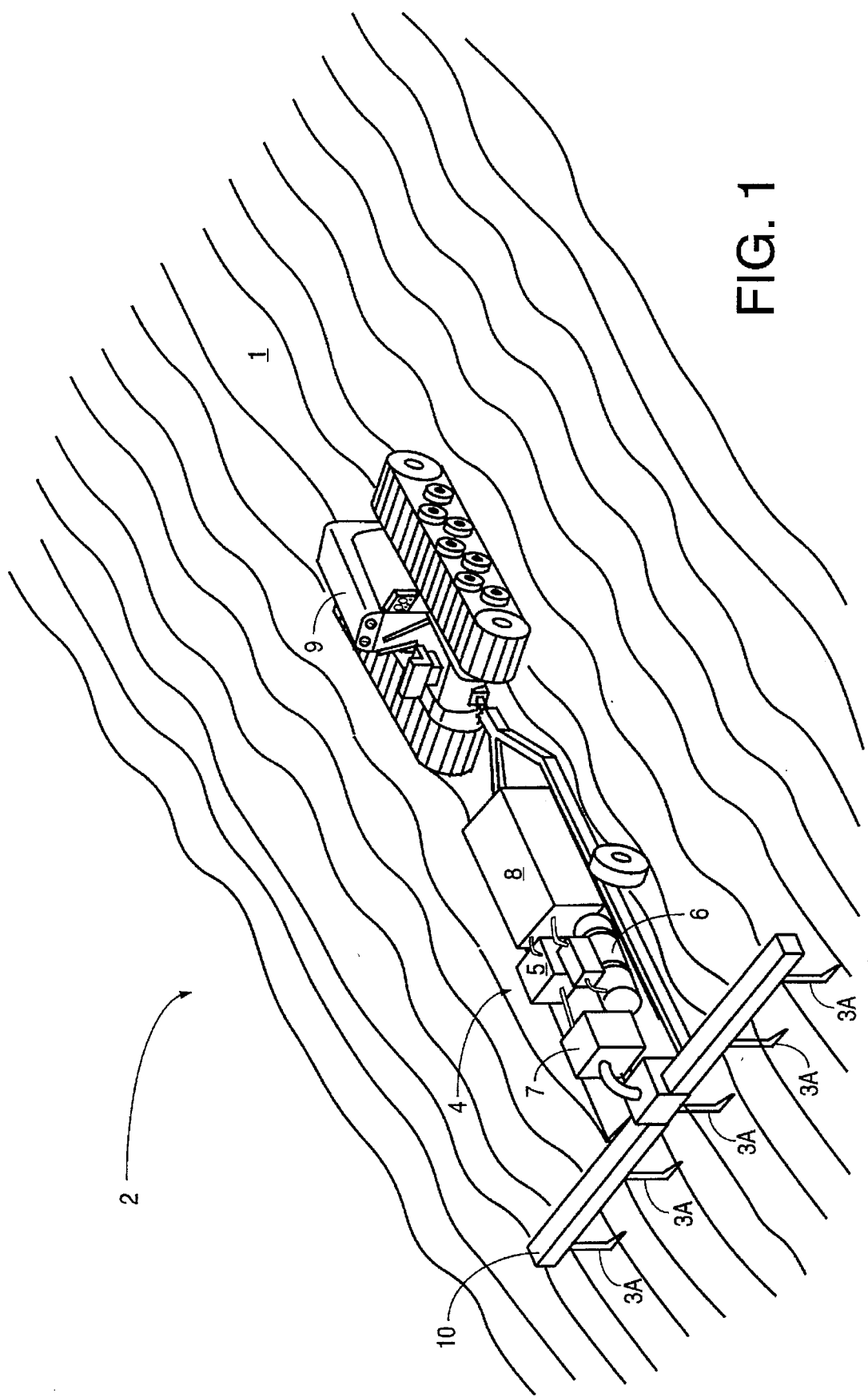
FIG. 1 illustrates an embodiment of a method and apparatus in accordance with this invention for ozone treatment of soil in a field.

FIG. 1 illustrates an embodiment of a method and apparatus in accordance with this invention for ozone treatment of soil 1 in a field 2. Field 2 is any space used for plant growth purposes including, but not limited to, open or cultivated fields, seed beds, orchards, or vineyards.

Soil 1 is any natural or artificial substance used for rooting and plant growth purposes such as clay, sand, rock or organic substrates. Soil 1 includes inorganic impurities and organic impurities such as biological organisms. In accordance with this invention, soil 1 is optionally rendered or ensured to be relatively uniformly homogenous in texture and free of clods and agglomerated clumps that inhibit free passage of a gas containing ozone through the soil. Conventional processes such as shanking, discing, tilling and springtoothing are typically used to render soil 1 in field 2 uniformly homogenous.

Prior to ozone treatment, soil 1 can be optionally allowed to dry or made to dry by various processes. Drying of soil may be necessary because of the difficulty in moving a gas through compact wet soil caused by water filling the interstitial spaces in the soil. After soil 1 is allowed to dry or made to dry, ozone containing gas is injected into soil 1 using a soil injector support device 10 to which soil injectors 3A are attached. Although FIG. 1 shows a number of soil injectors 3A for injecting the ozone containing gas into soil 1, any mechanism conventionally used in application of gases or liquids to soil can be used in accordance with this invention. In the embodiment of FIG. 1, soil injectors 3A are placed within a distance not exceeding three feet from the point in the soil at which sanitization is desired.

After injection, the ozone containing gas disperses through the interstitial spaces between the soil particles. Impurities in soil 1 including organic materials are oxidized by ozone. Ozone breaks down large complex organic molecules into smaller molecules and eventually into $H_2O$ and $CO_2$ or very small organic molecules. Ozone kills living cells and organisms in the soil by oxidizing the cell walls. When the cells in the soil are exposed to ozone for a sufficient period of time, lysing of cell walls occurs, releasing the cytoplasm of the cells and causing death of the cells.

In one embodiment in accordance with this invention, the following process parameters are associated with the use of ozone to kill biological life forms: (1) the soil's total moisture content at the moment of ozone treatment is less than or substantially equal to 15 percent by weight; (20 percent in another embodiment); (2) the soil and the ozone containing gas are at a temperature less than or substantially equal to 110 degrees Fahrenheit; (3) the ozone containing gas has a pressure greater than or substantially equal to 5.0 p.s.i. gauge pressure and an ozone concentration greater than or substantially equal to 0.1 percent by weight of the gas and (4) the ozone containing gas is injected to a depth greater than or substantially equal to 6 inches. The ozone containing gas is injected at various points in field 2 such that each injection point is at a distance less than or substantially equal to 3 feet from the farthest point at which sanitization is desired. For effective sanitization of the soil, soil 1 is exposed to the ozone containing gas for a period of time such that the result of multiplication of the ozone concentration and the time period is substantially equal to sixty parts per million-minutes.

Figure 2:
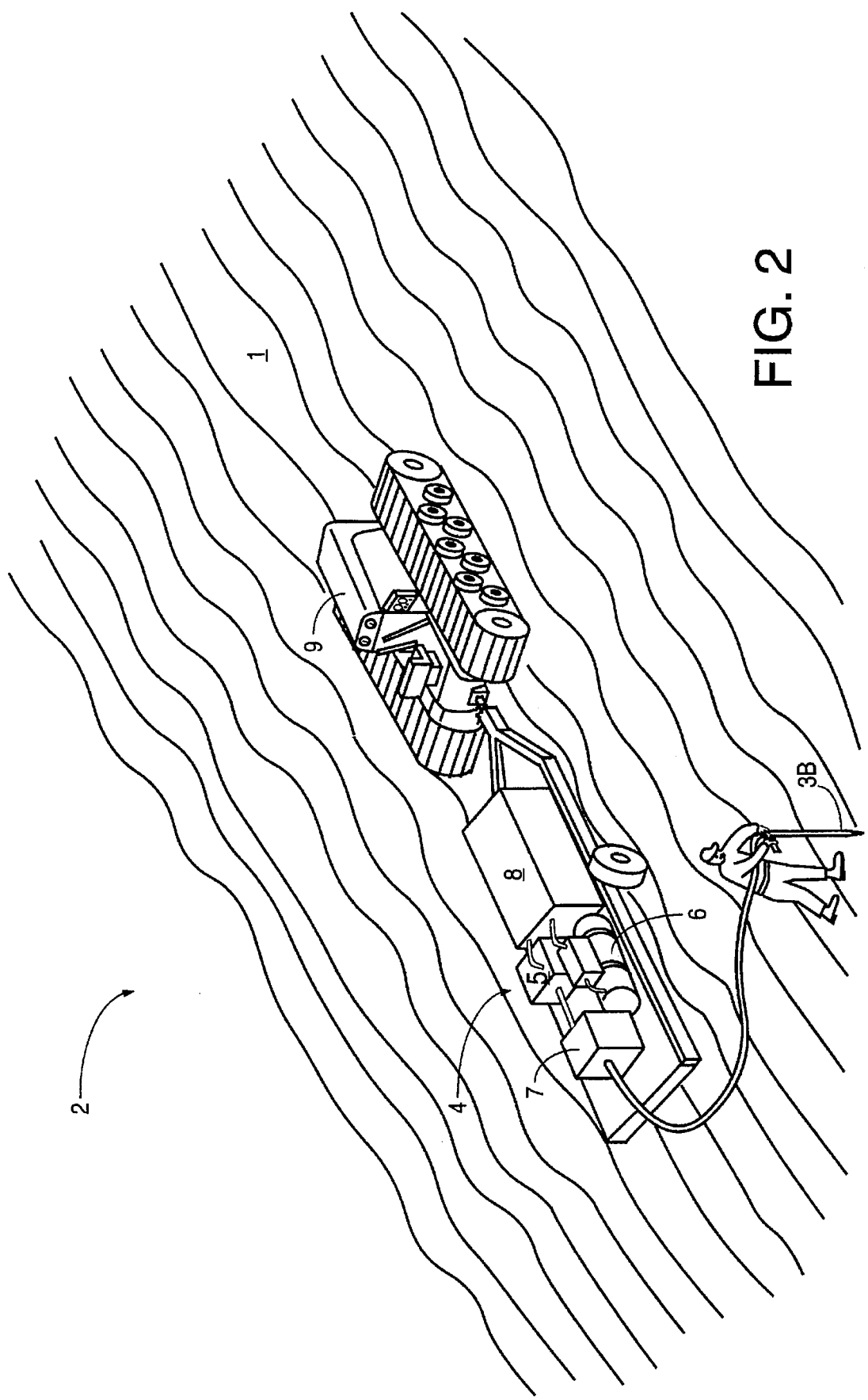
FIG. 2 illustrates an embodiment of a method and apparatus in accordance with this invention for ozone treatment of soil in a localized environment such as for a pretreatment for tree or vine replants.

The ozone containing gas is supplied to soil injector 3A or 3B from an ozone supplier 4. Ozone supplier 4 is any device used for supplying an ozone containing gas. For example, ozone supplier 4 can be a Hankin Ozotec model available from Hankin Atlas Ozone Systems in Scarborough, Ontario Canada. In one embodiment in accordance with this invention, ozone supplier 4 includes an electric generator 8, an ozone generator with power supply 7, an air compressor 6 and an air purification system 5 (FIGS. 1 and 2). An ozone supplier can also include an ozone chamber used to equalize pressure imbalances or mix or dilute the ozone containing gas with air.

As shown in FIG. 1, ozone supplier 4 is moved by a self propelled field device 9. Self propelled field device 9 can be replaced by any appropriate vehicle or equipment used for moving ozone supplier 4 relative to soil 1. The ozone supplier 4 is skid or trailer mounted and soil injector 3A is shanked into the ground. In accordance with this invention, an ozone supplier can be incorporated into a vehicle. Moreover, although FIG. 1 shows ozone containing gas being applied to soil in an open field, ozone containing gas can be used in any application in which sanitization is desired.

FIG. 2 illustrates an embodiment of a method and apparatus in accordance with this invention for manual localized in vivo ozone treatment of soil of some portion of a field. In FIG. 2, a worker is injecting ozone locally into the soil using a hand held injector 3B of the type shown in FIG. 3B. This apparatus is useful for example to inject ozone into localized regions of soil where it is not necessary or economical to treat by the apparatus shown in FIGS. 1 and 3A. A comparison of the lethal efficacy of the embodiment described in reference to FIG. 2 and FIG. 3B with the lethal efficacy shown by methyl bromide is presented in Table 1.

Figure 3A:
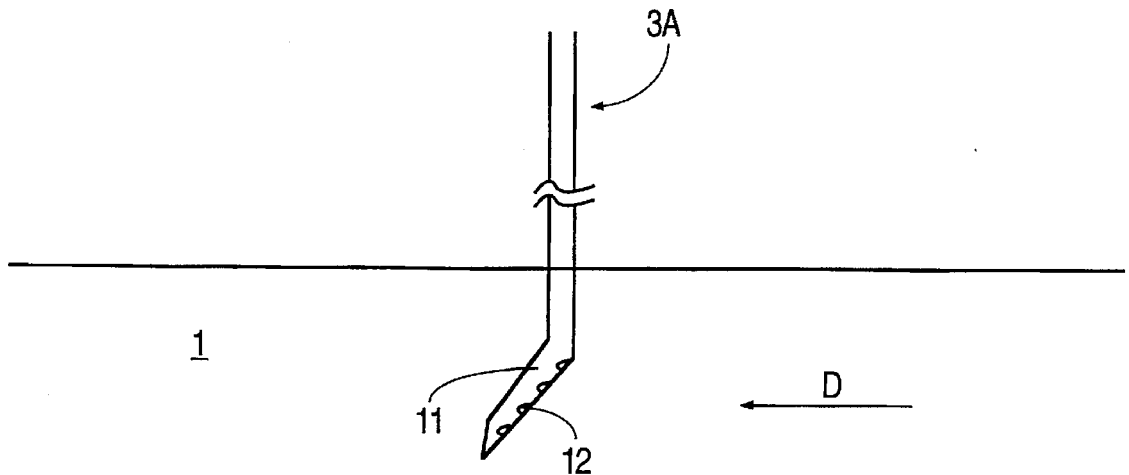
FIGS. 3A and 3B illustrate two embodiments of a soil injector for use in accordance with this invention.
Figure 3B:
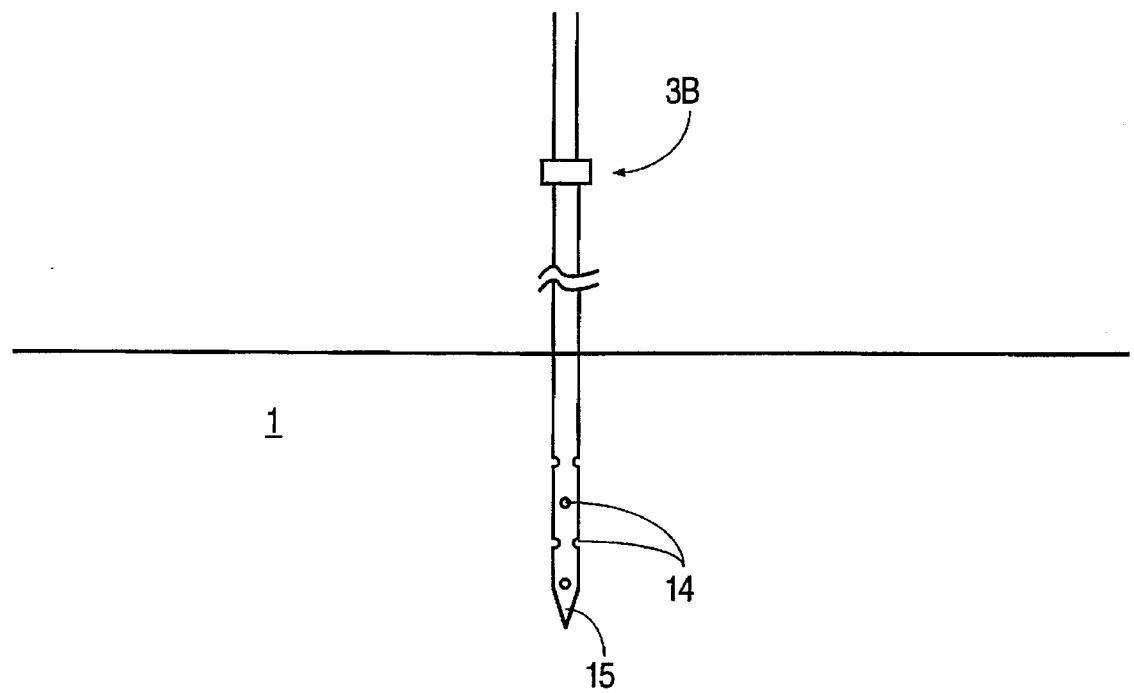

FIGS. 3A and 3B illustrate two embodiments of a soil injector for use in accordance with the invention. FIG. 3A shows an embodiment of soil injector 3A that can be used with a moving trailer. As shown in FIG. 3A, soil injector 3A is an extended hollow pipe with an angular end 11 bent in the direction of movement D and having one or more holes 12. Holes 12 are typically backward facing, opposite to direction D, or downward facing to prevent clogging of holes. FIG. 3B shows an embodiment of soil injector 3B that can be used manually for localized treatment. In the embodiment shown in FIG. 3B, soil injector 3B is an extended, hollow pipe, optionally with a sharpened end 15 to facilitate penetration of soil 1 for spot localized soil treatment (FIG. 2). Soil injector 3B has one or more holes 14 through which the ozone containing gas is injected into soil 1. Although two embodiments of soil injectors are illustrated in FIGS. 3A and 3B, any conventional soil injector can be used in accordance with this invention. Furthermore, a soil injector can be either stationary or moveable, permanent or temporarily placed in accordance with this invention.

Figure 4B:
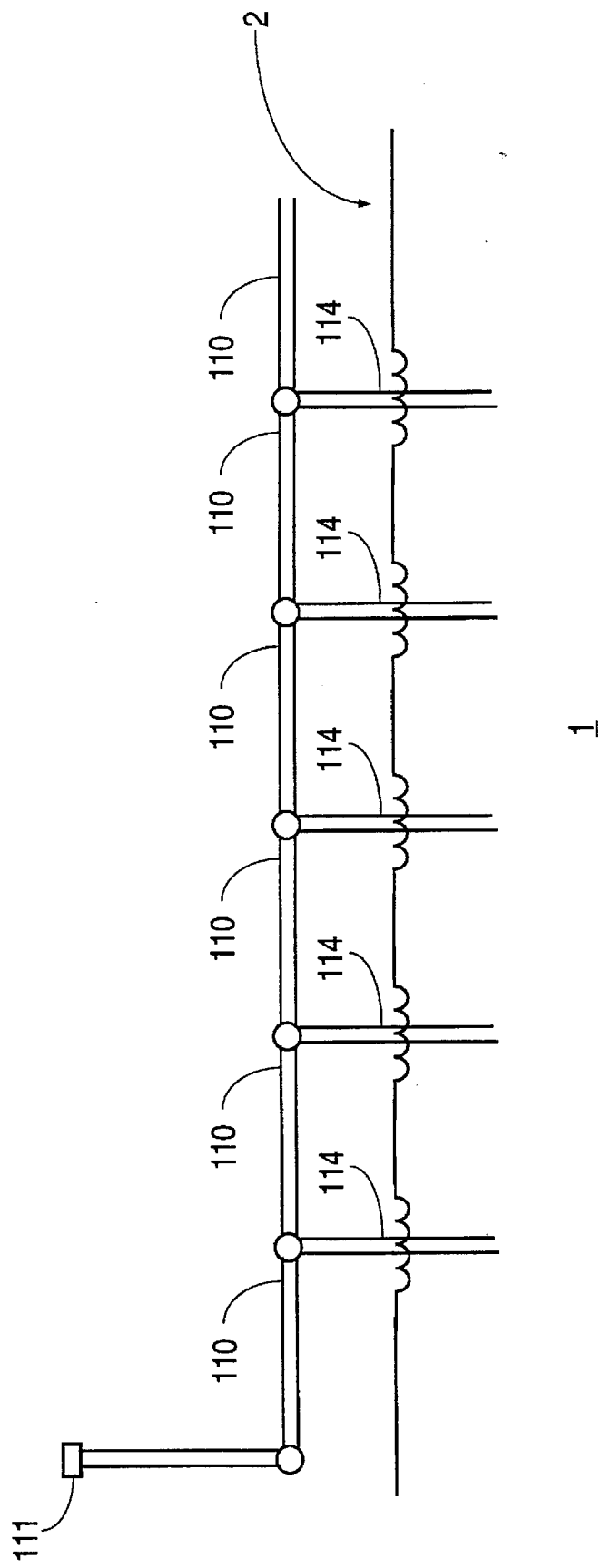

FIGS. 4A and 4B illustrates other embodiments of this invention for injecting an ozone containing gas into soil 1. As shown in FIG. 4A, an arrangement of hollow conduits 110 is buried under the surface of field 2. Although a generally rectangular lattice configuration of conduits 110 is illustrated in FIG. 4A, conduits 110 can be arranged in any manner appropriate for injecting a gas into the soil in accordance with this invention.

As shown in FIG. 4A, the ozone containing gas enters at conduit inlet 111 of the conduit lattice, is transmitted through conduits 110 and is injected into soil 1 through holes 112 in conduits 110 (see inset enlargement of conduit 110 in FIG. 4A). In one embodiment in accordance with this invention, conduits 110 are polyvinyl chloride (PVC) pipes. Furthermore, in accordance with this invention, conduits 110 can be used for other purposes such as underground irrigation or fertilization when conduits 110 are not used for injecting ozone containing gas into soil 1.

FIG. 4B shows an arrangement of hollow conduits 110 disposed horizontally on or over a surface of field 2 having a conduit inlet 111 and vertical conduits 114 with open ends inserted into soil 1. Conduit 114 can be a simple hollow conduit with an open end for discharging the gas. Alternatively, conduits 114 can be any conventional soil injector or one of 3A or 3B described above in reference to FIG. 3A or 3B.

Soil 1 is optionally covered with a gas impermeable or semi-impermeable membrane 113 (FIG. 4A) immediately subsequent or prior to injection of the ozone containing gas (tarping). Tarping serves to keep the ozone containing gas within soil 1 thus: (1) minimizing untoward detrimental emissions of ozone into the atmosphere, (2) minimizing ozone production costs and (3) resulting in a synergistic solarization effect. As used herein, the term "solarization" means the effect of tarping, or covering the soil to decrease heat losses from the soil to the atmosphere and to increase the ambient temperature of the soil due to the green-house effect. When combined with ozone treatment, tarping further reduces detrimental biological activity in soil 1. Although membrane 113 is shown only in FIG. 4A, membrane 113 can also be advantageously used in other embodiments such as FIGS. 1 and 2 in accordance with this invention. In such an embodiment, the tarping equipment may be manual or automatic and may be incorporated into the soil injector support device 10 carrying the soil injectors 3A (FIG. 1). A demonstration of the lethal efficacy of the lattice arrangement described above in reference to FIG. 4A is presented in Table 2.

Figure 5:
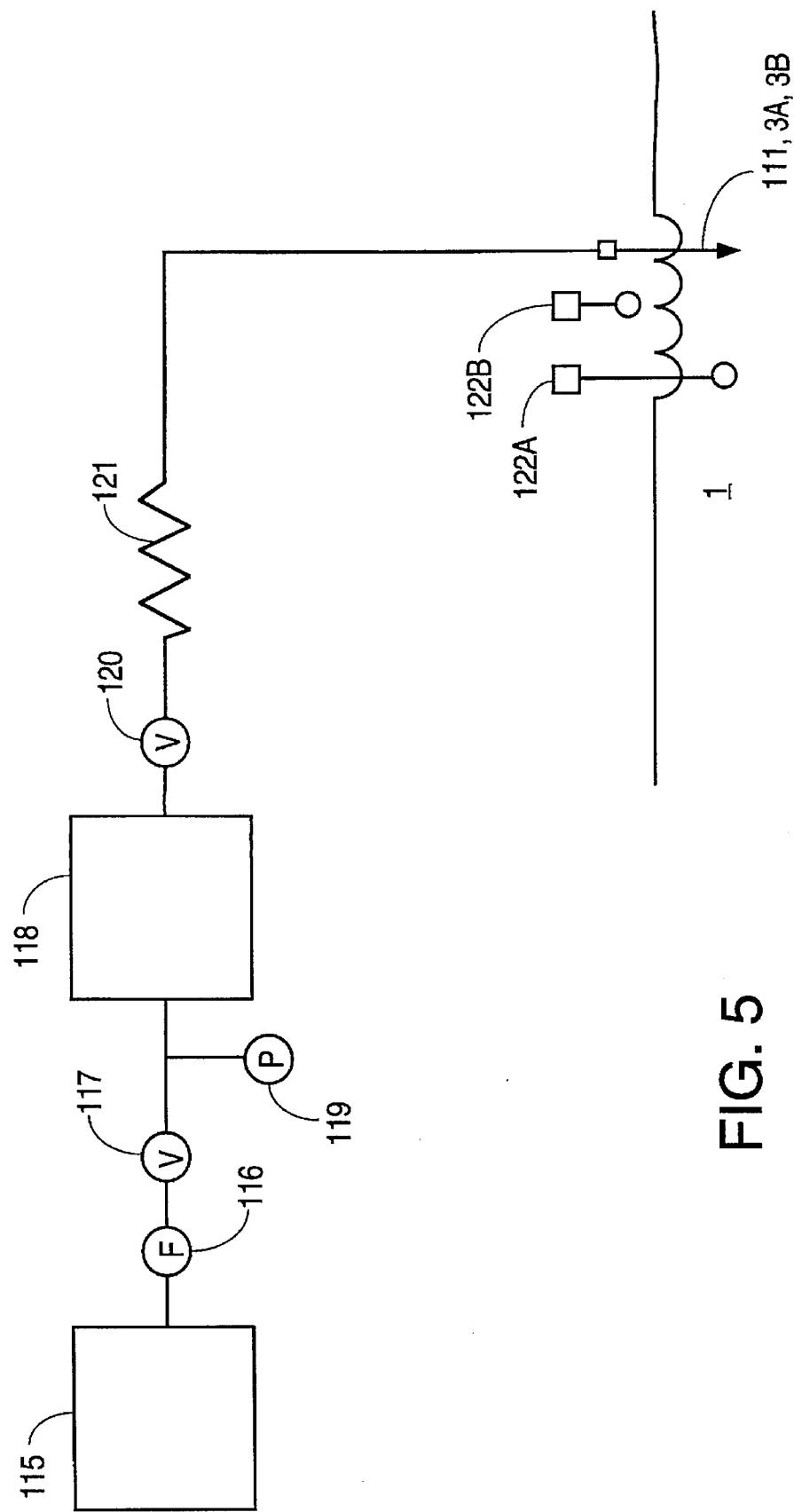
FIG. 5 illustrates a block diagram of a method and apparatus in accordance with this invention for the production of ozone containing gas.

FIG. 5 illustrates a block diagram of a method and apparatus for the production of ozone containing gas in accordance with this invention. Ozone can be made from air or from oxygen. Air yields a typical concentration of ozone by weight of up to 2%. Highly concentrated oxygen (90% to 98%) typically yields a concentration of ozone by weight up to 4% to 6%.

Using the equipment schematically illustrated in FIG. 5, dried oxygen containing gas is produced in chamber 115 by a conventional process such as refrigeration, pressure swing absorption, silica gel process, or membrane treatment process. The dried oxygen containing gas is supplied via a conduit to a filtering device 116 prior to generation of ozone. Filtering device 116 can be a particulate or hydrocarbon filter. One or more valves 117 control(s) the pressure of the dried purified oxygen containing gas to ozone generator 118, to optimize ozone output and limit over pressurization. Overpressurization, for example, may occur when the oxygen containing gas entering the ozone generator 118 exceeds 25 p.s.i.g. Valve 117 is a standard off the shelf pressure regulating valve. Ozone generator 118 can be a conventional corona ozone generator or one of a number of different variants. A pressure indicator device 119 is provided to monitor the pressure at which oxygen and other gases are introduced into the ozone generator and subsequently into soil injector 3 or lattice conduit inlet 111. A valve 120 controls the amount of ozone provided via conduit 121 to injector 3 or inlet 111. (See FIGS. 1, 2, 3A, 3B, 4A and 4B.) Conduit 121 can be a rigid conduit or a flexible conduit. An ozone gas concentration measuring device 122A is optionally provided in soil 1 at a distant point from the point of injection of the ozone containing gas to determine the actual concentration of ozone in soil 1. In the embodiments described in reference to FIGS. 2, 4A, and 4B, ozone gas concentration measuring device 122A is optionally placed between 6 inches and 3 feet from a point of ozone injection into the soil. Ozone gas concentration measuring device 122B is optionally provided to determine the amount of ozone emitted from soil 1 into the atmosphere. Concentration measurements from measuring device 122A or 122B can be used to estimate the end point of the ozone injection process for achieving the desired results. Ozone concentration measuring devices 122A and 122B can be any conventional devices such as available from Hankin Atlas Ozone Industries of Scarborough, Ontario, Canada.

In addition to the in-situ ozone treatment of soil described above, the soil may be treated in-vitro. In-vitro ozone treatment of soil may be necessary in greenhouse applications, in applications requiring greatly reduced ozone emissions for environmental reasons or for reducing damaging effects on other biological organisms in the field.

Figure 6:
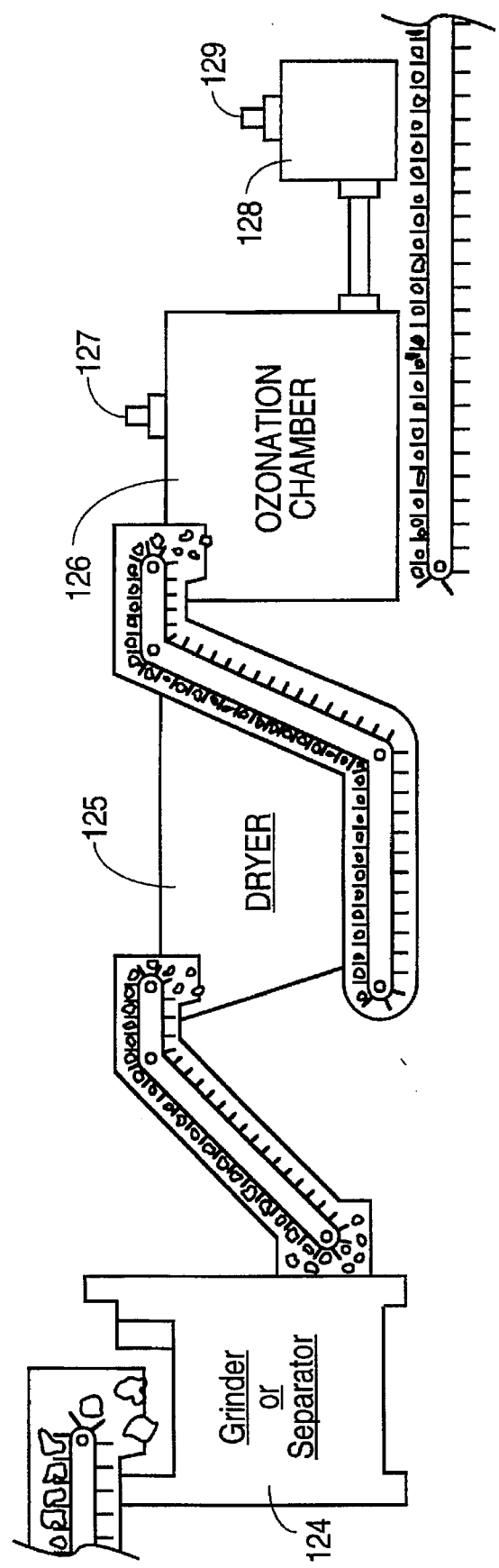
FIG. 6 illustrates a method and apparatus in accordance with this invention for in-vitro ozone treatment of soil.
Figure 7:
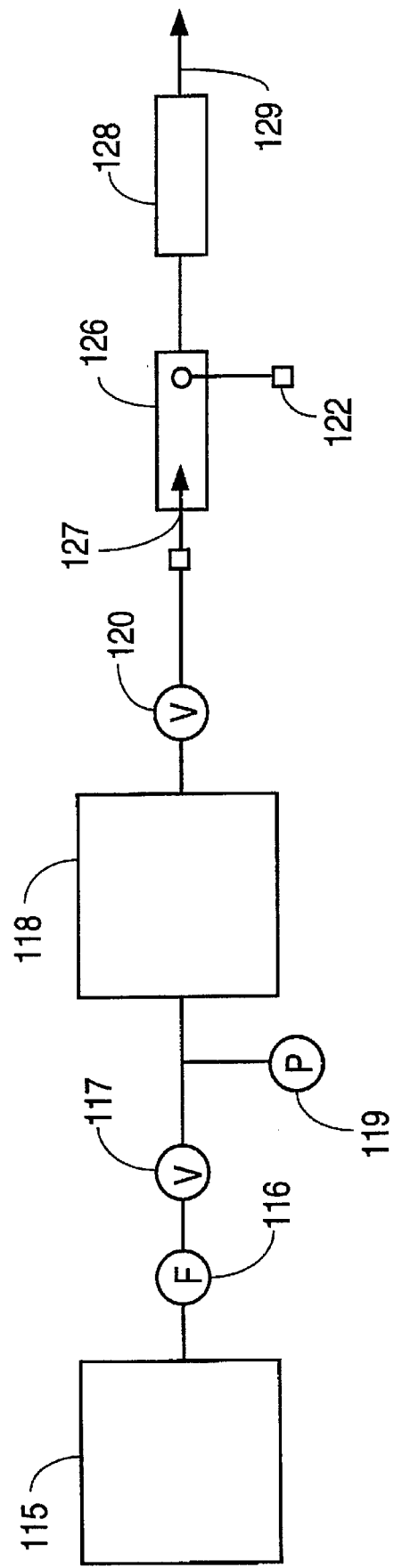
FIG. 7 illustrates a block diagram of the in-vitro ozone treatment apparatus and method shown in FIG. 6.

FIG. 6 illustrates a method and apparatus for in-vitro treatment of soil in accordance with this invention. FIG. 7 illustrates a block diagram of the in-vitro ozone treatment apparatus and method shown in FIG. 6. In the embodiment shown in FIGS. 6 and 7, the soil is removed from the field for in-vitro treatment. As shown in one embodiment of the invention in FIG. 6, the soil from a field optionally having clods and agglomerated clumps is optionally placed in an apparatus 124. Apparatus 124 can be a grinder or a separator that renders the soil relatively uniformly homogenous by conventional process such as grinding and mixing or screening and/or similar processing of the soil. The relatively uniform soil is then optionally transferred to a dryer 125 and dried until the total moisture content is less than or substantially equal to 15 percent. The dried soil is exposed to an ozone containing gas in ozonation chamber 126 at an ozone containing gas temperature or soil temperature less than or substantially equal to 110 degrees fahrenheit. The optimal maximum upper temperature is 110 degrees fahrenheit because ozone very rapidly reverts back into diatomic oxygen at temperatures substantially exceeding 110° F. Optimal ozone lifetimes are achieved when the temperature is minimized to the greatest extent possible. The soil temperature can even be below the freezing point of water. The ozone containing gas is supplied at inlet 127 of ozonation chamber 126 from an ozone generator 118 (FIG. 7). In FIGS. 6 and 7 ozonation chamber 126 is an enclosure which holds soil and into which ozone containing gas is injected. Ozonation chamber 126 of FIGS. 6 and 7 can be any size pipe or chamber with ozone going in at one end and out at the other end. The gases vented from ozonation chamber 126 are directed through a conduit to a deozonation chamber 128. Deozonation chamber 128 contains a catalyst to destroy any unconsumed ozone. The catalyst in deozonation chamber 128 can be activated carbon, manganese dioxide, or any other catalyst capable of destroying ozone or causing reversion of ozone to oxygen. Optionally, the vented gases may be heated to thermally destruct any ozone. The deozonated gases at outlet 129 of deozonator chamber 128 are environmentally safe and can be vented to the outside world. A demonstration of the lethal efficacy of the reductions in biological activity due to in-vitro treatment of soil in the manner described above in reference to FIGS. 6 and 7 is presented in Table 3.

As seen from Tables 1, 2 and 3, injection of sufficiently concentrated ozone containing gas at a relatively low pressure and temperature into relatively homogenous and dry soil and exposure of the soil-borne organisms to the ozone for a minimum period of time (dependent on the ozone concentration in the ozone containing gas) results in desirable reductions in biological activity in the soil. Furthermore, tarping maximizes sanitization of soil while simultaneously minimizing emissions of ozone gas into the atmosphere, minimizing the use of ozone and therefore reducing the expenditure of power otherwise necessary to produce the ozone gas. The slight positive increase in living organisms shown in some treatments in Tables 1, 2, and 3 can be due to the variability of the populations of living organisms in soils as compared to the untreated control soil samples. Therefore, treatment of soil with an ozone containing gas in accordance with this invention results in significant efficiency in reduction of living biological organisms in the soil. Ozone treatment of soil can also be used for soil decontamination caused by oil spills or excess pesticide/herbicide use.

The above description of various embodiments of this invention is intended to be merely illustrative and not limiting. Numerous other embodiments will be apparent to those skilled in the art, all of which are included in the broad scope of this invention. For example, soil injector 4 (FIG. 1) can be driven by pneumatic or hydraulic power. The scope of this invention is limited only by the appended claims.

TABLE 1

| Pounds of ozone or Methyl Bromide Injected (Tarped/Untarped) | Percent Change in Nematodes (per 500 g of Soil) at 1 foot from Injection Point | | Percent Change in Nematodes (per 500 g of Soil) at 3 feet from Injection Point |
| --- | --- | --- | --- |
| | Ozone | Methyl Bromide | Ozone |
| Control Tarped | 5 | −4 | 7 |
| Control Untarped | −1 | −8 | −4 |
| 0.07 Tarped | 7 | 5 | 0 |
| 0.07 Untarped | 5 | 9 | −13 |
| 0.22 Tarped | −15 | −45 | 8 |
| 0.22 Untarped | −5 | −35 | −18 |
| 0.7 Tarped | −55 | −85 | −7 |
| 0.7 Untarped | −40 | −86 | −16 |
| 2.2 Tarped | −86 | −98 | −15 |
| 2.2 Untarped | −78 | −92 | −10 |

Ozone Injected at 1.5% at 2–2.5 feet at 70 deg F. and 10 p.s.i

TABLE 2

| Pounds of Ozone Injected per 4 sq. ft. | Percent Change in Total Bacteria (per gram of Soil) |
| --- | --- |
| Control Tarped | −4 |
| Control Untarped | 6 |
| 0.1 Tarped | −11 |
| 0.1 Untarped | −2 |
| 0.5 Tarped | −15 |
| 0.5 Untarped | −12 |
| 2.5 Tarped | −82 |
| 2.5 Untarped | −68 |

Ozone Injected at 1.5% at 2.5 feet in 2 foot grid.

TABLE 3

| Ozone Gas Concentration (ppm) | Exposure Time (minutes) | Percent Change in Total Bacteria (per gram of Soil) |
| --- | --- | --- |
| Control | 60 | −5 |
| Control | 240 | 8 |
| 0.05 | 60 | −11 |
| 0.05 | 240 | −17 |
| 0.25 | 60 | 5 |
| 0.25 | 240 | −62 |
| 1 | 60 | −81 |
| 1 | 240 | −88 |
| 4 | 15 | −79 |
| 4 | 60 | −83 |
| 16 | 15 | −91 |
| 16 | 60 | −92 |

Ozone Injected at 70 deg F. and 10 p.s.i.

What is claimed is:

1. A process for killing living organisms in soil in a field, said process comprising:
   generating a gas, said gas comprising ozone ($O_3$);
   injecting said gas into said soil, said soil being suitable for plant growth purposes prior to said injecting, said soil including a plurality of living organisms, each of said living organisms comprising a cell, said cell comprising a cell wall, said injecting killing a number of living organisms in said plurality by oxidizing at least a portion of a cell wall of each living organism in said number.

2. The process of claim 1 wherein said soil of said field is exposed to ozone ($O_3$) for a period of time such that a result of multiplication of a concentration of said ozone ($O_3$) in said gas and said period of time is substantially equal to sixty parts per million-minutes.

3. The process of claim 1 wherein said soil of said field is exposed to ozone ($O_3$) for a period of time such that a result of multiplication of a concentration of said ozone ($O_3$) in said gas and said period of time is substantially greater than sixty parts per million-minutes.

4. The process of claim 1 wherein said ozone ($O_3$) is in a concentration substantially equal to 0.1 parts per million by weight of said gas.

5. The process of claim 1 wherein said ozone ($O_3$) is in a concentration substantially greater than 0.1 parts per million by weight of said gas.

6. The process of claim 1 further comprising a step of rendering said soil relatively homogenous in texture prior to said injection step.

7. The process of claim 1 further comprising a step of ensuring said soil is relatively homogenous in texture prior to said injection step.

8. The process of claim 1 wherein said soil is dried to substantially less than or equal to 20% moisture by weight prior to said injection step.

9. The process of claim 1 wherein said soil is allowed to dry to substantially less than or equal to 20% moisture by weight prior to said injection step.

10. The process of claim 1 further comprising a step of covering said soil with a gas impermeable membrane.

11. The process of claim 1 further comprising a step of covering said soil with a gas semipermeable membrane.

12. The process of claim 1, wherein said gas consists essentially of ozone and a carrier gas, said process further comprising:
    moving an ozone supplier over said surface of said field.

13. The process of claim 1, wherein said gas is injected at a depth greater than or substantially equal to six inches and less than or substantially equal to three feet from a surface of said field.

14. The process of claim 13, wherein said gas consists essentially of ozone and a carrier gas, said process further comprising:
    moving an ozone supplier over said surface of said field.

15. The process of claim 13, wherein said soil of said field is exposed to ozone ($O_3$) for a period of time such that a result of multiplication of a concentration of said ozone in said gas and said period of time is substantially greater than sixty parts per million-minutes.

16. The process of claim 13 further comprising a step of rendering said soil relatively homogenous in texture prior to said injection step.

17. The process of claim 13 further comprising a step of covering said soil with a gas impermeable membrane.

\* \* \* \* \*